United States Patent
Morcos

(10) Patent No.: US 10,245,744 B2
(45) Date of Patent: Apr. 2, 2019

(54) ACCESSORY FOR OSCILLATING POWER TOOLS

(71) Applicant: Cherif Morcos, Kirkland (CA)

(72) Inventor: Cherif Morcos, Kirkland (CA)

(73) Assignee: Cherif Morcos, Kirkland, Quebec (CA)

( * ) Notice: Subject to any disclaimer, the term of this patent is extended or adjusted under 35 U.S.C. 154(b) by 93 days.

(21) Appl. No.: 15/238,491

(22) Filed: Aug. 16, 2016

(65) Prior Publication Data

US 2016/0354945 A1 Dec. 8, 2016

Related U.S. Application Data

(63) Continuation of application No. 12/932,728, filed on Mar. 7, 2011, now abandoned.

(60) Provisional application No. 61/316,294, filed on Mar. 22, 2010.

(51) Int. Cl.
*B26D 7/26* (2006.01)
*A61B 17/14* (2006.01)

(52) U.S. Cl.
CPC ............... *B26D 7/26* (2013.01); *A61B 17/14* (2013.01)

(58) Field of Classification Search
CPC ... Y10T 83/9377; Y10T 83/9379; B26D 7/26; B26D 7/2614; A61B 17/14; A61B 17/142
USPC ............................. 30/394, 393; 606/176, 178
See application file for complete search history.

(56) References Cited

U.S. PATENT DOCUMENTS

| 21,984,444 | | 4/1940 | Swanson |
| 3,103,069 | A | 9/1963 | Gary |
| 4,058,317 | A | 11/1977 | McCarthy |
| 4,637,391 | A * | 1/1987 | Schlein .................... A61F 15/02 30/133 |
| 4,657,428 | A | 4/1987 | Wiley |
| 5,048,366 | A | 9/1991 | Spanio |

(Continued)

OTHER PUBLICATIONS

Restriction Requirement dated Oct. 26, 2017 in connection with Design U.S. Appl. No. 29/574,523.

(Continued)

*Primary Examiner* — Phong H Nguyen

(57) ABSTRACT

An accessory for an oscillating power tool is provided. The accessory has a body having a functional portion for performing work and an attachment portion for mounting the accessory to the oscillating power tool. An arbor, defined at the attachment portion of the body, is configured to matingly engage attachment elements of a drive flange of a variety of manufacturers' oscillating power tools. The arbor comprises a plurality of openings including a primary opening comprising a central opening defining a central axis of the arbor, a first elongated opening conjoined with the central opening and extending radially from the central axis along a first radial axis and a second elongated opening conjoined with the central opening and extending radially from the central axis along a second radial axis. The plurality of openings also includes a set of secondary openings disjoined from the primary opening and positioned radially about the central axis along respective radial axes. The accessory can fit, with no loss of functionality, oscillating power tools' connectors from multiple manufacturers. The accessory may be a blade, a rasp, a sander, a scraper or any other accessory for oscillating power tools, in any material such as metal, plastic, or other.

21 Claims, 6 Drawing Sheets

(56) References Cited

U.S. PATENT DOCUMENTS

| | | |
|---|---|---|
| 5,496,316 A | 3/1996 | Goris |
| 7,217,177 B2 | 5/2007 | Frech et al. |
| D633,928 S * | 3/2011 | Nilsson ........................ D15/138 |
| D651,062 S | 12/2011 | Wackwitz |
| D651,499 S | 1/2012 | Tong |
| D651,874 S | 1/2012 | Davidian et al. |
| D651,875 S | 1/2012 | Davidian et al. |
| D651,876 S | 1/2012 | Davidian et al. |
| D651,877 S | 1/2012 | Davidian et al. |
| D651,878 S | 1/2012 | Davidian et al. |
| D652,274 S | 1/2012 | Davidian et al. |
| D677,546 S | 3/2013 | Zhou et al. |
| D682,652 S | 5/2013 | McRoberts et al. |
| D693,193 S | 11/2013 | Bozic |
| D694,076 S | 11/2013 | Davidian et al. |
| D694,077 S | 11/2013 | Bozic |
| D694,596 S | 12/2013 | Davidian et al. |
| D694,597 S | 12/2013 | Davidian et al. |
| D694,598 S | 12/2013 | Davidian et al. |
| D694,599 S | 12/2013 | Davidian et al. |
| D697,384 S | 1/2014 | Wackwitz |
| D709,341 S | 7/2014 | Nispel |
| D724,923 S | 3/2015 | McRoberts et al. |
| D735,568 S | 8/2015 | Barnett |
| D741,135 S | 10/2015 | Yang et al. |
| D741,136 S | 10/2015 | Yang et al. |
| 9,186,770 B2 | 11/2015 | Montplaisir et al. |
| D744,800 S | 12/2015 | Cooksey et al. |
| D750,461 S | 3/2016 | McRoberts et al. |
| 2002/0070037 A1 | 6/2002 | Jasch |
| 2002/0112589 A1 | 8/2002 | Lee et al. |
| 2008/0190259 A1 | 8/2008 | Bohne |
| 2010/0056029 A1 | 3/2010 | Grunikiewicz |
| 2011/0076927 A1 | 3/2011 | Ho |
| 2011/0277611 A1 | 11/2011 | Chen et al. |
| 2011/0316241 A1 | 12/2011 | Zhang et al. |
| 2011/0316242 A1 | 12/2011 | Zhang et al. |
| 2012/0311876 A1 | 12/2012 | Zhang |
| 2014/0190328 A1 | 7/2014 | Karlen |

OTHER PUBLICATIONS

Office Action issued in connection with U.S. Appl. No. 12/932,728 dated Nov. 29, 2012—8 pages.

Final Office Action issued in connection with U.S. Appl. No. 12/932,728 dated Mar. 15, 2013—7 pages.

Office Action issued in connection with U.S. Appl. No. 12/932,728 dated Jul. 26, 2013—7 pages.

Final Office Action Action issued in connection with U.S. Appl. No. 12/932,728 dated Jun. 16, 2014—9 pages.

Examiner's Answer issued in connection with U.S. Appl. No. 12/932,728 dated Mar. 2, 2015—15 pages.

Response to Arguments issued in connection with U.S. Appl. No. 12/932,728 dated Jun. 1, 2015—5 pages.

Office Action dated Apr. 4, 2018 in connection with Design U.S. Appl. No. 29/574,523—7 pages.

* cited by examiner

ACCESSORY FOR OSCILLATING POWER TOOLS

CROSS REFERENCE TO RELATED APPLICATIONS

This application is a continuation claiming the benefit of priority under 35 U.S.C. § 120 based on co-pending U.S. patent application Ser. No. 12/932,728, which was filed on Mar. 7, 2011, which itself claimed the benefit of priority under 35 USC 119(e) based on U.S. Provisional Patent Application No. 61/316,294 filed on Mar. 22, 2010. The contents of each of these applications are incorporated herein by reference in their entirety.

FIELD OF THE INVENTION

The invention relates generally to accessories for power tools, and more particularly, to accessories such as blades, rasps, sanders, scrapers and the like that can be secured to a drive flange of oscillating power tools for use therewith.

BACKGROUND

Oscillating power tools may be used in combination with different types of accessories (e.g., blades, rasps, sanders, scrapers) in order to perform different desired tasks. The accessories are typically configured to be releasably fastened to and removed from the oscillating power tool to either replace a used accessory with a newer one and/or to attach a different type of accessory to the oscillating power tool to perform a different function. Manufacturers of these oscillating power tools often sell such accessories with the caveat that the accessories are specifically designed for exclusive use with their brand of oscillating power tool and are therefore incompatible with other manufacturers' oscillating power tools.

This may be more easily understood with reference to a specific example.

U.S. Patent Application Publication 2008/0190259 to Bohne ("Bohne"), which is part of the prior art, describes an example of a prior art accessory 14 (e.g., a blade) mountable to an oscillating power tool 28, as shown in FIGS. 1A and 1B. More specifically, as is common for oscillating power tools, the accessory 14 is mounted to a drive flange 38 of the oscillating power tool 28 via a fastening portion 44 of the accessory 14 which has a number of form-locking elements 12' (i.e., openings) for engaging a number of form-locking elements 12 (i.e., projections) of the drive flange 38. Once the accessory 14 is engaged with the drive flange 38 in that manner, a screw 42 is engaged with a threaded hole 10 of the drive flange 38 to clamp the accessory 14 against the drive flange 38.

In order to ensure that only their accessories are compatible with their oscillating power tools, manufacturers configure the projections on the drive flanges of their oscillating power tools (such as the form-locking elements 12 of Bohne) to have a specific pattern with which only their respective accessories are matable. As a result, users that own oscillating power tools made by different manufacturers are required to hold stock of each individual oscillating power tool's requisite replacement accessories due to the accessories' respective arbor (i.e., a fitting slot/hole—such as the form-locking elements 12' of Bohne) that is unique to each manufacturer. This results in high inventories of blades and/or other types of accessories which can be costly to maintain, particularly since some accessories, such as blades, provided by these manufacturers are expensive. Moreover and in particular with respect to blades, due to this high associated cost, users tend to stretch the use of manufacturers' blades beyond a point of usefulness (i.e., after they've become dull).

In light of the above, it is apparent that there is a need in the industry to provide blades and other accessories for oscillating power tools which are compatible with oscillating power tools made by different manufacturers.

SUMMARY

In accordance with a first aspect, a blade accessory for use with an oscillating power tool is provided. The blade accessory comprises a body extending in a longitudinal direction from a first end to a second end. The first end of the body is a blade end for cutting and the second end of the body is an attachment end for mounting the blade accessory to the oscillating power tool. The blade accessory also comprises an arbor defined at the attachment end of the body. The arbor is configured to matingly engage attachment elements of a drive flange of the oscillating power tool. The arbor comprises a plurality of openings including a primary opening which comprises: a central opening which defines a central axis of the arbor; a first elongated opening conjoined with the central opening and extending radially from the central axis along a first radial axis; and a second elongated opening conjoined with the central opening and extending radially from the central axis along a second radial axis. The second radial axis is substantially orthogonal to the first radial axis. The plurality of openings further includes a set of secondary openings disjoined from the primary opening and positioned radially about the central axis along respective radial axes distinct from the first and second radial axes.

In accordance with another aspect, an accessory for use with an oscillating power tool is provided. The accessory comprises a body having a functional portion for performing work and an attachment portion for mounting the accessory to the oscillating power tool. The accessory further comprises an arbor defined at the attachment portion of the body. The arbor is configured to matingly engage attachment elements of a drive flange of the oscillating power tool. The arbor comprises a plurality of openings including a primary opening which comprises: a central opening defining a central axis of the arbor; a first elongated opening conjoined with the central opening and extending radially from the central axis along a first radial axis; and a second elongated opening conjoined with the central opening and extending radially from the central axis along a second radial axis. The second radial axis is substantially orthogonal to the first radial axis. The plurality of openings further includes a set of secondary openings disjoined from the primary opening and positioned radially about the central axis along respective radial axes.

In accordance with another aspect, an accessory for use with an oscillating power tool is provided. The accessory comprises a body having a functional portion for performing work and an attachment portion for mounting the accessory to the oscillating power tool. The accessory further comprises an arbor defined at the attachment portion of the body. The arbor is configured to matingly engage attachment elements of a drive flange of the oscillating power tool. The arbor comprises a plurality of cavities including a primary cavity which comprises: a central cavity defining a central axis of the arbor; a first elongated cavity conjoined with the central opening and extending radially from the central axis along a first radial axis; and a second elongated cavity conjoined with the central cavity and extending radially from the central axis along a second radial axis. The second radial axis is substantially orthogonal to the first radial axis. The plurality of cavities further includes a set of secondary cavities disjoined from the primary cavity and positioned radially about the central axis along respective radial axes.

The arbor of the blade or other accessory presented here differs from previously used arbors because it can fit, with no loss of functionality, the drive flange of oscillating power tools made by many major manufacturers.

The arbor may be used in connection with blades, rasps, sanders, scrapers or any other attachment for power oscillating tools in any material such as metal, plastic, or other.

The cavities of the arbor are defined in order to fit many of the major power oscillating tool manufacturer's devices.

The arbor includes opening and/or embossed/de-bossed portions that allow for attachments made of metal, plastic, or other, to fit onto the oscillating power tool's drive flange. The end of the attachment can serve as either a blade to cut, a sander to sand, a rasp to sand, a scraper to scrape, or a grout remover to remove grout with power assistance from the power oscillating tool. The attachment fits tightly to provide functionality, maintain torque, and is secured by the arbor, and a screw or fastener on the other side of the drive flange.

Other aspects of the invention include design components that make the accessory comprising the arbor unique. The above summary of the present disclosure is not intended to describe every implementation of the present disclosure. The figures and the detailed description that follow more particularly exemplify these implementations.

Figure 1A:
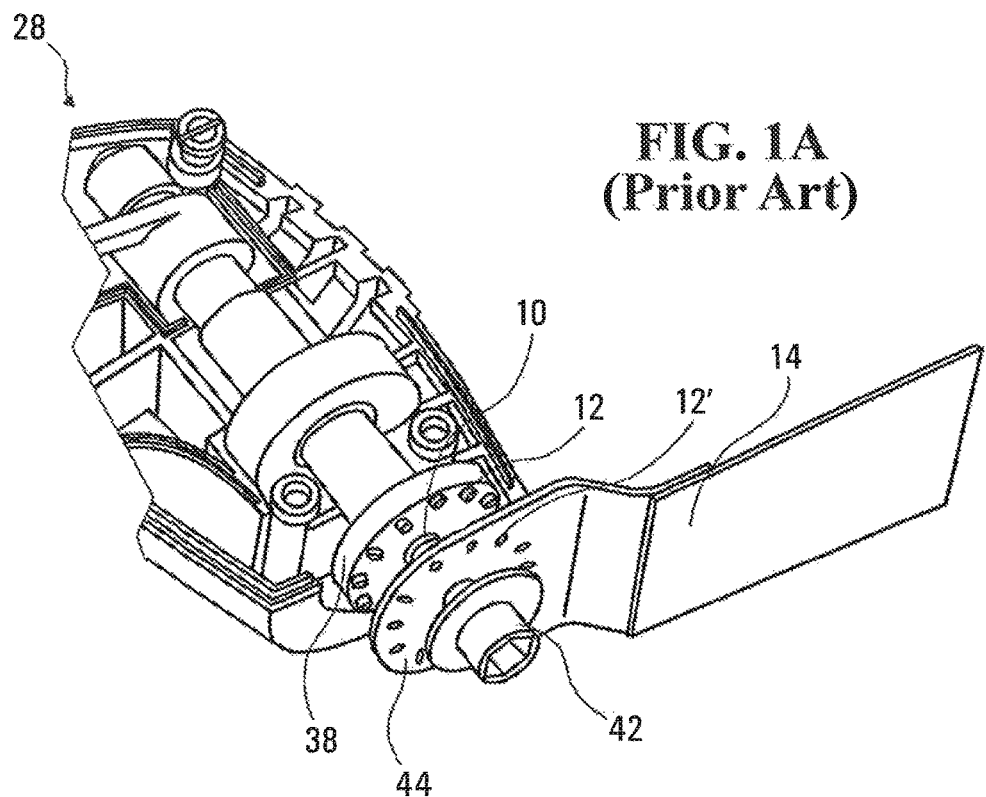
FIG. 1A shows a prior art accessory being mounted to a drive flange of an oscillating power tool.
Figure 1B:
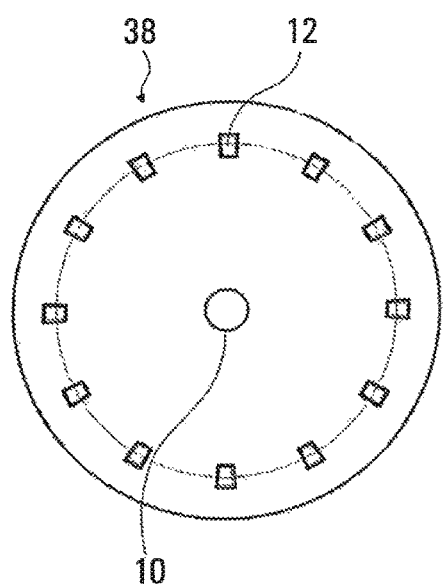
FIG. 1B shows a pattern of projections defined in the drive flange of the oscillating power tool shown in FIG. 1A.

In the drawings, embodiments of the invention are illustrated by way of examples. It is to be expressly understood that the description and drawings are only for the purpose of illustration and are an aid for understanding. They are not intended to be a definition of the limits of the invention.

DETAILED DESCRIPTION

Figure 2A:
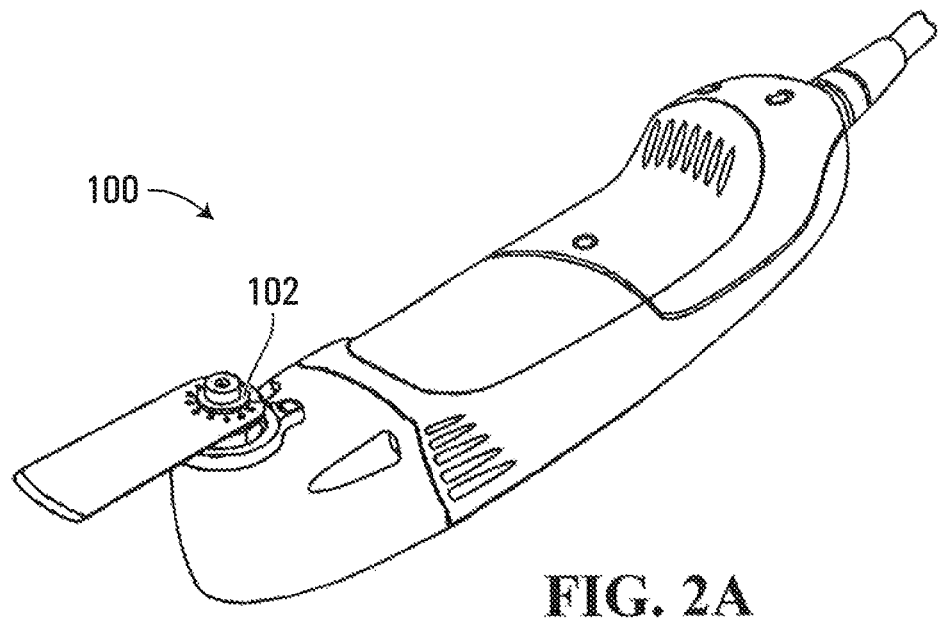
FIGS. 2A and 2B show top and bottom perspective views of another example of an oscillating power tool to which is mounted another prior art accessory.
Figure 2B:
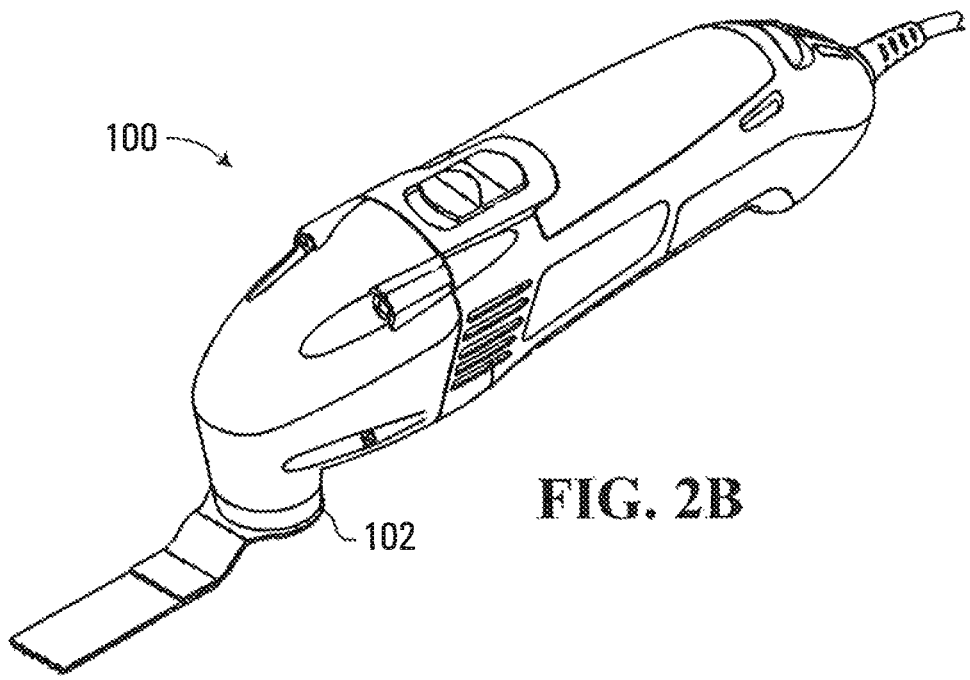
Figure 3:
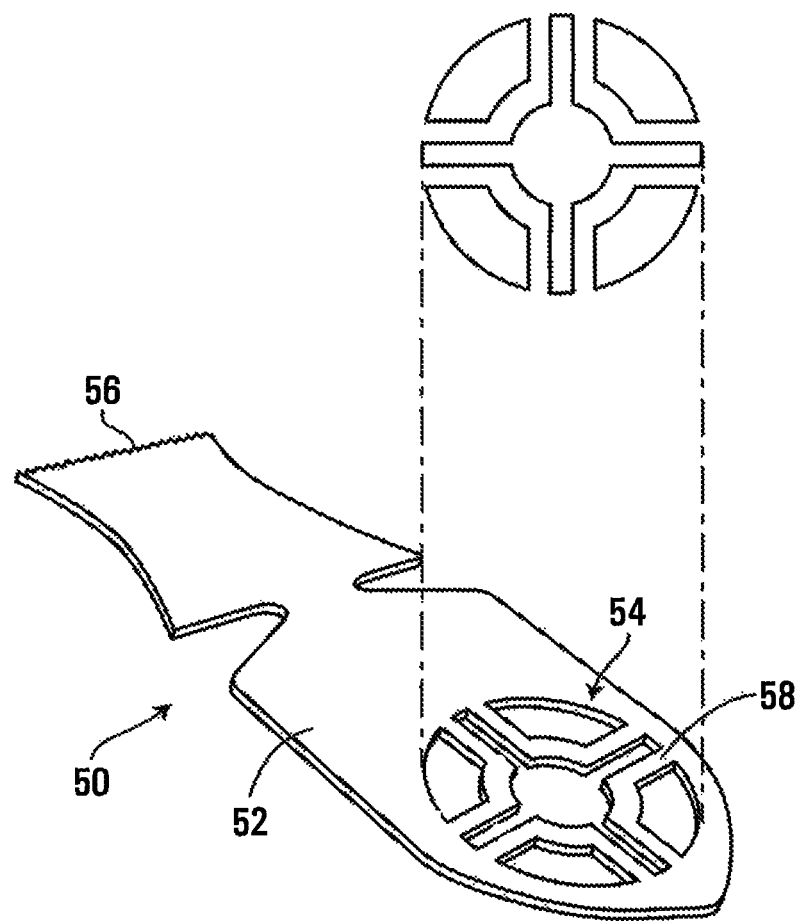
FIG. 3 is a perspective view of an accessory for an oscillating power tool, in this example a blade accessory, in accordance with a specific embodiment of the invention.

FIG. 3 shows an example of an accessory 50 for use with an oscillating power tool 100 in accordance with an embodiment of the invention. The oscillating power tool 100, shown in FIGS. 2A and 2B, comprises a drive flange 102 for mounting the accessory 50 thereto. In this embodiment, the accessory 50 is a blade accessory used for cutting. The blade 50 comprises a body 52 and an arbor 54 defined in the body 52 for matingly engaging attachment elements (e.g., projections) of the drive flange 102 of the oscillating power tool 100.

As will be discussed in more detail below, the blade 50 may be mounted onto oscillating power tools produced by a variety of manufacturers despite the fact that these manufacturers design the drive flanges of their oscillating power tools to have different patterns of projection in order to be solely compatible with their own accessories. Notably, as discussed above, replacement blades for manufacturers' oscillating power tools are only provided by those manufacturers for use with their specific oscillating power tool and could not be used with other manufacturers' oscillating power tools.

As discussed above, this common practice can result in users being required to hold stock of each individual oscillating power tool's requisite replacement blades due to an arbor (i.e., a fitting slot/hole) of the accessory that is unique to each manufacturer's oscillating power tool. This results in higher cost and higher blade inventories than what could be allowed under a "universal" arbor (i.e., an arbor that is compatible with a multitude of manufacturers' oscillating power tools).

Continuing with FIG. 3, the body 52 of the blade 50 extends in a longitudinal direction from a first end 56 to a second end 58. The first end 56 of the body 52 is a functional end that allows the accessory 50 to perform its function (i.e., cutting). As such, in this embodiment, the first end 56 is a blade end that allows the blade 50 to cut. For instance, in this example, the blade end 56 comprises cutting teeth. The second end 58 is an attachment end for mounting the blade 50 to the drive flange 102 of the oscillating power tool 100. More specifically, the attachment end 58 defines the arbor 54 which is configured to matingly engage attachment elements (e.g., projections) of the drive flange 102 of the oscillating power tool 100.

The body 52 of the blade 50 is made of a material 62. The material 62 may be, for example, a metallic material, a plastic material or any other suitable material.

The arbor 54 can be thought of as being "universal" as it is compatible, with no loss of functionality, with the drive flanges (sometimes referred to as "receptacles") of the oscillating power tools of multiple manufacturers.

Figure 4:
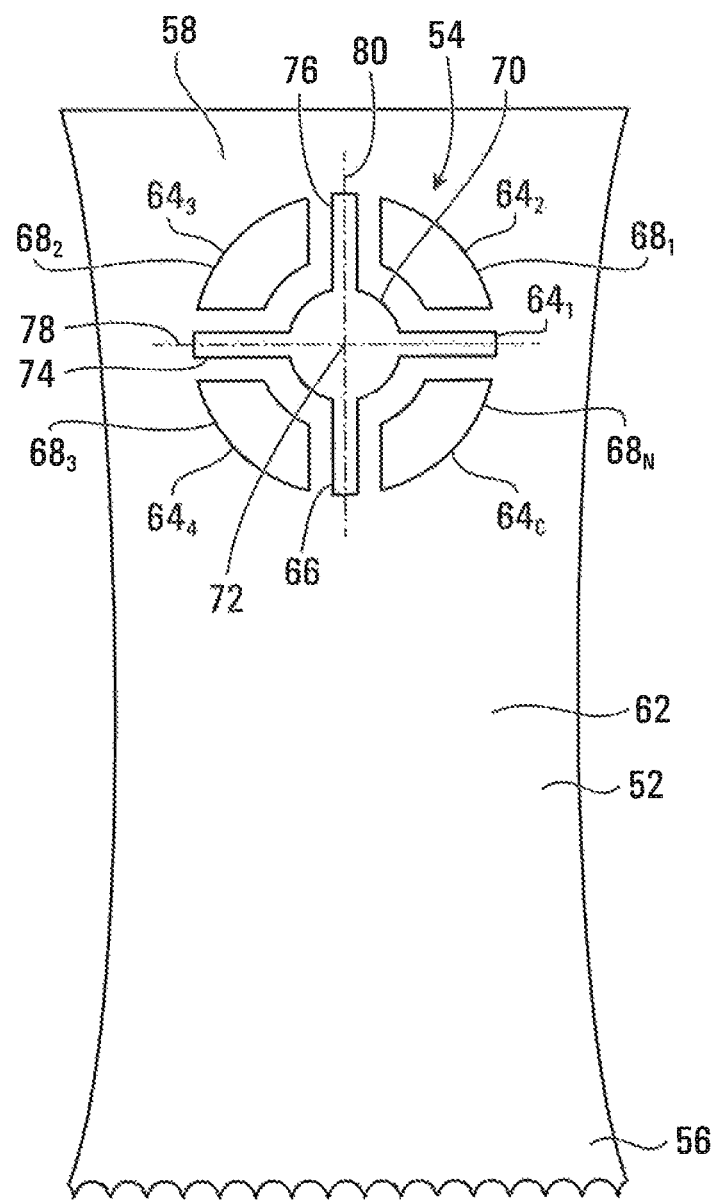
FIG. 4 is a front view of another example of a blade in accordance with another embodiment of the invention.

To that end, and as can best be seen in FIG. 4, the arbor 54 comprises a plurality of cavities $64_1$-$64_C$ which are configured to receive the attachment elements of the drive flange 102 of the oscillating power tool 100. In this embodiment, the plurality of cavities $64_1$-$64_C$ includes a primary cavity 66 which is centrally located amongst the plurality of cavities $64_1$-$64_C$, and a set of secondary cavities $68_1$-$68_N$ positioned radially about the primary cavity 66. In this embodiment, the cavities $64_1$-$64_C$ are in the form of openings in that they traverse the body 52 of the blade 50 from one face of the blade 50 to another. However, in other embodiments, the cavities $64_1$-$64_C$ may be depressed or raised portions of the body 12 (e.g., debossed or embossed portions).

The primary opening 66 comprises a central opening 70 which defines a central axis 72 of the arbor 54, and first and second elongated openings 74, 76 each conjoined with the central opening 70 and extending radially from the central axis 72. More particularly, the first elongated opening 74 extends from the central axis 72 along a first radial axis 78 while the second elongated opening 76 extends from the central axis 72 along a second radial axis 80 transversal to the first radial axis 78. In particular, the second radial axis 80 is substantially orthogonal to the first radial axis 78. The primary opening 66 may thus be considered to be generally cross-shaped with a generally circular opening located at the intersection of the two arms of the cross. Moreover, in this embodiment, the second radial axis 80 lies along the longitudinal direction of the body 52 of the blade 50.

Figure 5:
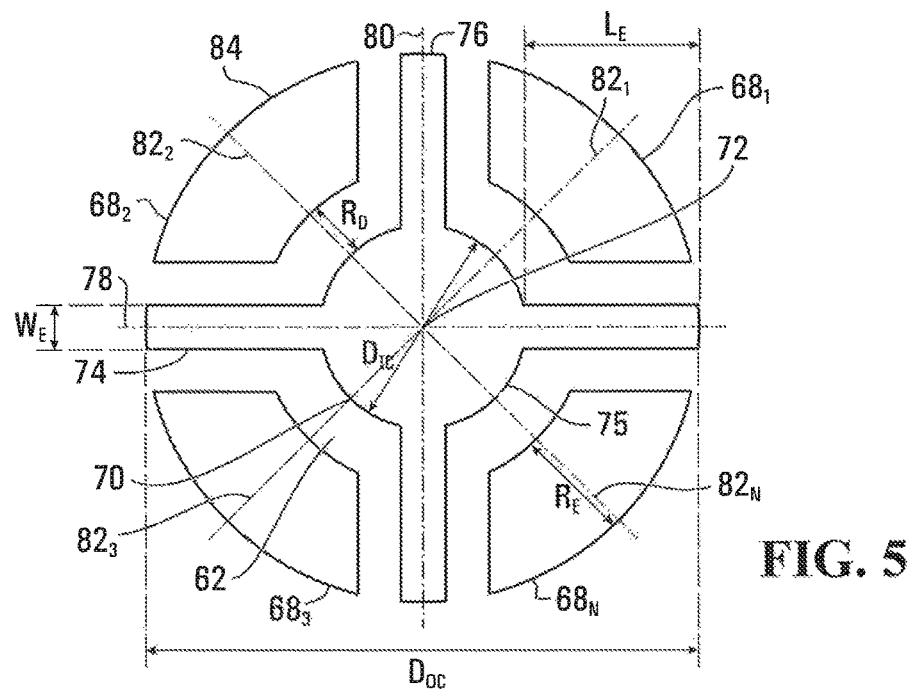
FIG. 5 is a diagrammatic view of an arbor of the blade of FIG. 4 in which the arbor comprises a plurality of cavities, including a primary cavity and a set of secondary cavities.

Characteristics of the cavities of the arbour 54 may be better appreciated with reference to FIG. 5. As depicted, the first and second elongated openings 74, 76 are generally rectangular and each has a width $W_E$ of about 2 mm measured in a direction normal to the first and second radial axes 78, 80. Moreover, each of the first and second elongated openings 74, 76 extends from the central opening 70 by a length $L_E$ of about 7.5 mm. For its part, the central opening 70 has a generally circular shape which defines an inner circle 75 of the arbor 54. The inner circle 75 has a diameter $D_{IC}$ of about 10 mm.

The secondary openings $68_1$-$68_N$ are disjoined from (i.e., not connected to) the primary opening 66 such that the material 62 of the body 52 separates the secondary openings $68_1$-$68_N$ from the primary opening 66. More particularly, at least some of the secondary openings $68_1$-$68_N$ are separated from the central opening 70 by a radial distance $R_D$ of about 3.25 mm. Moreover, the secondary openings $68_1$-$68_N$ are positioned radially about the central axis 72 along respective radial axes $82_1$-$82_N$ distinct from the first and second radial axes 78, 80 of the first and second elongated openings 74, 76.

Figure 6A:
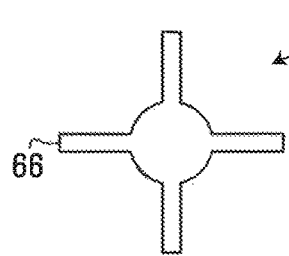
FIG. 6A shows a variant of the arbor of FIG. 4 in which the plurality of cavities of the arbor includes a primary cavity but no secondary cavities.
Figure 6B:
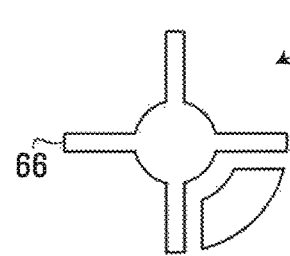
FIG. 6B shows another variant of the arbor of FIG. 4 in which the set of secondary cavities includes one secondary cavity.
Figure 6C:
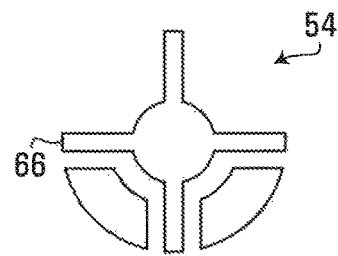
FIG. 6C shows another variant of the arbor of FIG. 4 in which the set of secondary cavities includes two secondary cavities.
Figure 6D:
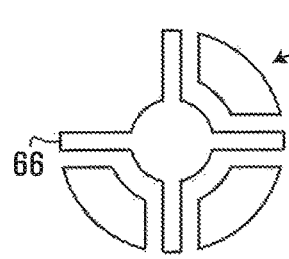
FIG. 6D shows another variant of the arbor of FIG. 4 in which the set of secondary cavities includes three secondary cavities.
Figure 6E:
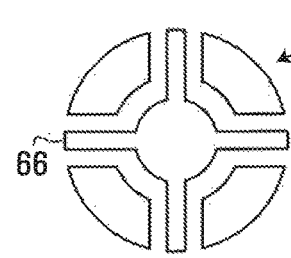
FIG. 6E shows another variant of the arbor of FIG. 4 in which the set of secondary cavities includes four secondary cavities.
Figure 6F:
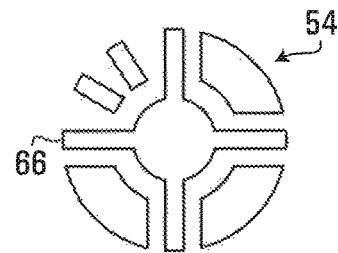
FIG. 6F shows another variant of the arbor of FIG. 4 in which the set of secondary cavities includes five secondary cavities.
Figure 6G:
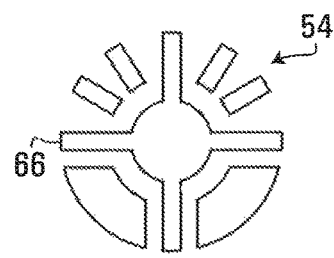
FIG. 6G shows another variant of the arbor of FIG. 4 in which the set of secondary cavities includes six secondary cavities.
Figure 6H:
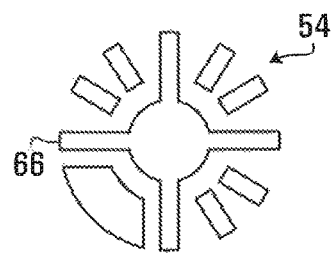
FIG. 6H shows another variant of the arbor of FIG. 4 in which the set of secondary cavities includes seven secondary cavities.
Figure 6I:
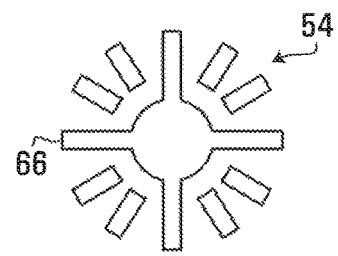
FIG. 6I shows another variant of the arbor of FIG. 4 in which the set of secondary cavities includes eight secondary cavities.
Figure 6J:
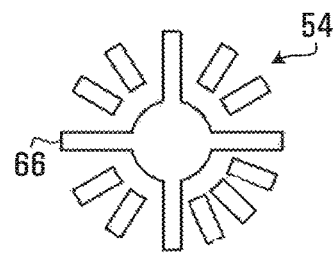
FIG. 6J shows another variant of the arbor of FIG. 4 in which the set of secondary cavities includes nine secondary cavities.
Figure 6K:
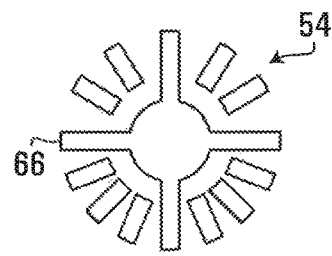
FIG. 6K shows another variant of the arbor of FIG. 4 in which the set of secondary cavities includes ten secondary cavities.
Figure 6L:
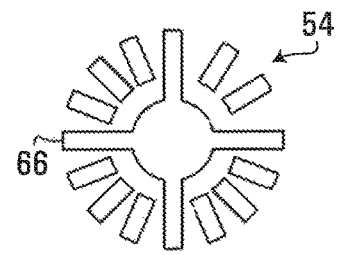
FIG. 6L shows another variant of the arbor of FIG. 4 in which the set of secondary cavities includes eleven secondary cavities.
Figure 6M:
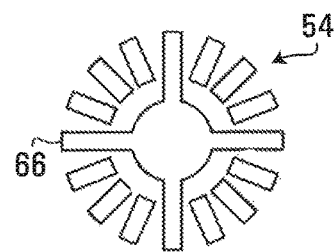
FIG. 6M shows another variant of the arbor of FIG. 4 in which the set of secondary cavities includes twelve secondary cavities.

While in the embodiments depicted in FIGS. 4 and 5, the set of secondary openings $68_1$-$68_N$ includes four secondary openings, the set of secondary openings $68_1$-$68_N$ may include more or fewer secondary openings in other embodiments as depicted in FIG. 6A to 6M. For instance, the set of secondary openings $68_1$-$68_N$ may include at least one secondary opening, in some cases at least two separate secondary openings, in some cases at least four separate secondary openings, and in some cases even more. For example, the set of secondary openings $68_1$-$68_N$ may include twelve separate secondary openings, as shown in FIG. 6M.

The primary opening 66 and the set of secondary openings $68_1$-$68_N$ form a substantially circular shape defining an outer circle 84 of the arbor 54. In specific practical implementations, the outer circle 84 has a diameter $D_{OC}$ of about 25 mm. At least some of the secondary openings $68_1$-$68_N$ extend to define part of a periphery of the outer circle 84. As such, at least some of the secondary openings $68_1$-$68_N$ have a radial extent $R_E$ of about 4.25 mm.

The blade accessory 50, via the configuration of its arbor 54, notably its openings $64_1$-$64_C$, is compatible with the major manufacturers' oscillating power tools with no loss of functionality at a price that will allow for replacement of dulling blades when required, as opposed to stretching the use of manufacturers' blades beyond a point of usefulness (i.e., after they've become dull) due to their cost. In connection with the specific design depicted in FIG. 5, the arbor 54 may allow the blade 50 to be placed at angles up to every 30 degrees in a circle when mounted onto the drive flange of may oscillating power tools.

Looking to FIG. 5, and in a specific implementation, the arbor 54 of the blade accessory has the following dimensions, expressed within a range of greater than or less than 1 mm for all measurements:

A) Outer circle 84 diameter $D_{OC}$: 25 mm
B) Inner circle 75 diameter $D_{IC}$: 10 mm
C) Radius distance from outer limit of middle circle to outer circle $R_E$: 4.25 mm
D) Primary opening 66: first (x-axis)—78: 25 mm, second (y-axis) 80: 25 mm, 2 mm width ($W_E$)
E) Radial distance $R_D$ between central opening 70 and secondary openings $68_1$-$68_N$: 3.25 mm It will be understood that while the accessory 50 has been described and shown as a blade accessory in this embodiment, in other embodiments, the accessory 50 may be a rasp, a sander, a scraper, a grout remover or any other accessory for oscillating power tools in any material such as metal, plastic, or other. For example, the functional end 56 of the accessory 50 can serve as either a blade to cut, a sander to sand, a rasp to sand, a scraper to scrape, or a grout remover to remove grout with power assistance from the oscillating power tool. In specific practical implementations, the accessory 50 may be configured to fit tightly onto the flange 102 of the oscillating power tool 100 to provide functionality, maintain torque, and is secured by the arbor 54, and a screw or fastener on the other side of the drive flange 102 of the oscillating power tool 100.

The above specification, and examples provide a complete description of the use of the invention. Since many embodiments of the invention can be made without departing from the spirit and scope of the invention, the invention is defined by the claims.

What is claimed is:

1. A blade accessory for use with an oscillating power tool, the blade accessory comprising:
a body extending in a longitudinal direction from a first end to a second end, the first end being a blade end for cutting, the second end being an attachment end for mounting the blade accessory to the oscillating power tool;

an arbor defined at the attachment end of the body, the arbor being configured to matingly engage attachment elements of a drive flange of the oscillating power tool, the arbor comprising a plurality of openings including:
a primary opening comprising:
a central opening defining a central axis of the arbor;
a first elongated opening conjoined with the central opening and extending radially from the central axis along a first radial axis;
a second elongated opening conjoined with the central opening and extending radially from the central axis along a second radial axis, wherein said second radial axis is substantially orthogonal to said first radial axis;
wherein the first elongated opening and the second elongated opening each extend radially to a first specific radial distance measured from the central axis of the arbor; and
a set of secondary openings disjoined from said primary opening and positioned radially about the central axis along respective radial axes distinct from said first and second radial axes, the secondary openings in the set of secondary openings extending to a second specific radial distance measured from the central axis of the arbor, wherein the second specific radial distance to which the secondary openings extend is the same as the first specific radial distance to which the first and second elongated openings extend.

2. The blade accessory of claim 1, wherein the set of secondary openings includes at least one secondary opening.

3. The blade accessory of claim 1, wherein the set of secondary openings includes at least two separate secondary openings.

4. The blade accessory of claim 1, wherein the set of secondary openings includes at least four separate secondary openings.

5. The blade accessory of claim 1, wherein the second radial axis along which extends the second elongated opening lies along the longitudinal direction of the body of the blade accessory.

6. The blade accessory of claim 1, wherein the first and second elongated openings are generally rectangular.

7. The blade accessory of claim 6, wherein each of the first and second elongated openings has a width of about 2 mm.

8. The blade accessory of claim 1, wherein the primary opening and the set of secondary openings of the arbor jointly define at least part of a substantially circular periphery of the arbor, the at least part of the substantially circular periphery being at a distance corresponding to the first specific radial distance measured from the central axis of the arbor to which the first and second elongated openings extend.

9. The blade accessory of claim 8, wherein the substantially circular periphery is characterized by a diameter of about 25 mm.

10. The blade accessory of claim 9, wherein the central opening has a substantially circular shape defining an inner circle of the arbor.

11. The blade accessory of claim 10, wherein the inner circle of the arbor defined by the central opening has a diameter of about 10 mm.

12. The blade accessory of claim 11, wherein the first elongated opening radially extends from the central opening along the first radial axis by a length of about 7.5 mm and wherein the second elongated opening radially extends from the central opening along the second radial axis by a length of about 7.5 mm.

13. The blade accessory of claim 8, wherein at least some of the secondary openings have radial extents of about 4.25 mm.

14. The blade accessory of claim 8, wherein at least some of the secondary openings are separated from the central opening by a radial distance of about 3.25 mm.

15. The blade accessory of claim 1, wherein the blade end of the body of the blade accessory comprises cutting teeth.

16. The blade accessory of claim 1, wherein the blade accessory is made of a metallic material.

17. An accessory for use with an oscillating power tool, the accessory comprising:
a body having a functional portion for performing work and an attachment portion for mounting the accessory to the oscillating power tool;
an arbor defined at the attachment portion of the body, the arbor being configured to matingly engage attachment elements of a drive flange of the oscillating power tool, the arbor comprising a plurality of openings including:
a primary opening comprising:
a central opening defining a central axis of the arbor;
a first elongated opening conjoined with the central opening and extending radially from the central axis along a first radial axis;
a second elongated opening conjoined with the central opening and extending radially from the central axis along a second radial axis, wherein said second radial axis is substantially orthogonal to said first radial axis;
wherein the first elongated opening and the second elongated opening each extend radially to a first specific radial distance measured from the central axis of the arbor; and
a set of secondary openings disjoined from said primary opening and positioned radially about the central axis along respective radial axes distinct from said first and second radial axes, the secondary openings in the set of secondary openings extending to a second specific radial distance measured from the central axis of the arbor wherein the second specific radial distance to which the secondary openings extend is the same as the first specific radial distance to which the first and second elongated openings extend.

18. The accessory of claim 17, wherein the accessory is one of a blade, a scraper, a sander, a rasp and a grout remover.

19. An accessory for use with an oscillating power tool, the accessory comprising:
a body having a functional portion for performing work and an attachment portion for mounting the accessory to the oscillating power tool;
an arbor defined at the attachment portion of the body, the arbor being configured to matingly engage attachment elements of a drive flange of the oscillating power tool, the arbor comprising a plurality of cavities including:
a primary cavity comprising:
a central cavity defining a central axis of the arbor;
a first elongated cavity conjoined with the central cavity and extending radially from the central axis along a first radial axis;
a second elongated cavity conjoined with the central cavity and extending radially from the central axis along a second radial axis, wherein said second radial axis is substantially orthogonal to said first radial axis;

wherein the first elongated cavity and the second elongated cavity each extend radially to a first specific radial distance measured from the central axis of the arbor; and a set of secondary cavities disjoined from said primary cavity and positioned radially about the central axis along respective radial axes distinct from said first and second radial axes, the secondary openings in the set of secondary openings extending to a second specific radial distance measured from the central axis of the arbor, wherein the second specific radial distance to which the secondary openings extend is the same as the first specific radial distance to which the first and second elongated openings extend.

20. The accessory of claim 19, wherein the cavities in the set of secondary cavities are openings that traverse the body.

21. The accessory of claim 19, wherein the cavities in the set of secondary cavities depressed portions of the body of the accessory.

\* \* \* \* \*